US007871649B2

(12) United States Patent
Modak et al.

(10) Patent No.: US 7,871,649 B2
(45) Date of Patent: *Jan. 18, 2011

(54) ANTIMICROBIAL COMPOSITIONS CONTAINING SYNERGISTIC COMBINATIONS OF QUATERNARY AMMONIUM COMPOUNDS AND ESSENTIAL OILS AND/OR CONSTITUENTS THEREOF

(75) Inventors: Shanta M. Modak, River Edge, NJ (US); Milind S. Shintre, New York, NY (US); Trupti Gaonkar, New York, NY (US); Lauserpina Caraos, Hollis, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 421 days.

This patent is subject to a terminal disclaimer.

(21) Appl. No.: 10/891,624

(22) Filed: Jul. 15, 2004

(65) Prior Publication Data
US 2005/0019431 A1 Jan. 27, 2005

Related U.S. Application Data

(60) Provisional application No. 60/488,349, filed on Jul. 17, 2003, provisional application No. 60/530,864, filed on Dec. 18, 2003.

(51) Int. Cl.
*A01N 65/00* (2009.01)
(52) U.S. Cl. .................................................. 424/736
(58) Field of Classification Search ........................ None
See application file for complete search history.

(56) References Cited

U.S. PATENT DOCUMENTS

| 3,257,276 A | 6/1966 | Broh-Kahn et al. |
| 3,485,915 A | 12/1969 | Gerstien et al. |
| 3,960,745 A | 6/1976 | Billany et al. |
| 4,243,657 A | 1/1981 | Okumura et al. |
| 4,318,907 A | 3/1982 | Kligman et al. |
| 4,393,076 A | 7/1983 | Noda et al. |
| 4,478,853 A | 10/1984 | Chaussee et al. |
| 4,587,266 A | 5/1986 | Verdicchio |
| 4,604,384 A | 8/1986 | Smith et al. |
| 4,814,334 A * | 3/1989 | Salkin |
| 4,853,978 A | 8/1989 | Stockum |
| 4,868,169 A | 9/1989 | O'Laughlin et al. |
| 4,870,108 A | 9/1989 | Page |
| 4,889,844 A | 12/1989 | Silvetti, Sr. et al. |
| 4,910,205 A | 3/1990 | Kogan et al. |
| 4,919,837 A | 4/1990 | Gluck |
| 4,956,170 A | 9/1990 | Lee et al. |
| 4,963,591 A | 10/1990 | Fourman et al. |
| 4,966,754 A | 10/1990 | Purohit et al. |
| 5,031,245 A | 7/1991 | Milner |
| 5,059,416 A | 10/1991 | Cherukuri et al. |
| 5,073,372 A | 12/1991 | Turner et al. |
| 5,089,205 A | 2/1992 | Huang et al. |
| 5,110,809 A | 5/1992 | Wang et al. |
| 5,116,602 A | 5/1992 | Robinson et al. |
| 5,133,090 A | 7/1992 | Modak et al. |
| 5,147,648 A | 9/1992 | Bannert |
| 5,164,107 A | 11/1992 | Khan et al. |
| 5,208,031 A | 5/1993 | Kelly |
| 5,357,636 A | 10/1994 | Dresdner, Jr. et al. |
| 5,403,864 A | 4/1995 | Bruch et al. |
| 5,447,930 A | 9/1995 | Nayak |
| 5,516,510 A | 5/1996 | Beilfuss et al. |
| 5,591,442 A | 1/1997 | Diehl et al. |
| 5,599,549 A | 2/1997 | Wivell et al. |
| 5,612,324 A * | 3/1997 | Guang Lin et al. |
| 5,624,675 A | 4/1997 | Kelly |
| 5,624,962 A | 4/1997 | Takeuchi et al. |
| 5,648,389 A | 7/1997 | Gans et al. |
| 5,658,575 A | 8/1997 | Ribier et al. |
| 5,705,532 A | 1/1998 | Modak et al. |
| 5,708,023 A | 1/1998 | Modak et al. |
| 5,736,574 A | 4/1998 | Burnier et al. |
| 5,750,122 A * | 5/1998 | Evans et al. |
| 5,753,270 A * | 5/1998 | Beauchamp et al. |
| 5,776,430 A | 7/1998 | Osborne et al. |
| 5,804,203 A | 9/1998 | Hahn et al. |
| 5,830,488 A | 11/1998 | Suzuki et al. |
| 5,885,562 A | 3/1999 | Lowry et al. |
| 5,888,562 A | 3/1999 | Hansen et al. |

(Continued)

FOREIGN PATENT DOCUMENTS

DE    4140474    6/1993

(Continued)

OTHER PUBLICATIONS

Lawless, Julia. The Illustrated Encyclopedia of Essential Oils: The Complete Guide to the Use of Oils in Aromatherapy and Herbalism. Element Books, 1995, USA. pp. 132, 162-164, 169, 223, 227 and 228.*

(Continued)

*Primary Examiner*—Michele Flood
(74) *Attorney, Agent, or Firm*—Baker Botts LLP

(57) ABSTRACT

The present invention relates to compositions comprising quaternary ammonium compounds and essential oils or individual constituents thereof which exhibit enhanced antimicrobial effects. Such combinations may be comprised in lotions, gels, creams, soaps, etc. for application to skin or mucous membranes. The invention is based, at least in part, on the observation that synergistic antimicrobial effects are achieved with combinations of essential oils or individual constituents thereof and low concentrations of quaternary ammonium compounds.

7 Claims, No Drawings

U.S. PATENT DOCUMENTS

| | | | |
|---|---|---|---|
| 5,902,572 A | 5/1999 | Luebbe et al. |
| 5,906,808 A | 5/1999 | Osborne et al. |
| 5,951,993 A | 9/1999 | Scholz et al. |
| 5,965,137 A | 10/1999 | Petrus |
| 5,965,610 A | 10/1999 | Modak et al. |
| 5,980,477 A | 11/1999 | Kelly |
| 5,980,925 A | 11/1999 | Jampani et al. |
| 5,985,918 A * | 11/1999 | Modak et al. |
| 5,985,931 A | 11/1999 | Modak et al. |
| 6,022,551 A | 2/2000 | Jampani et al. |
| 6,037,386 A | 3/2000 | Modak et al. |
| 6,040,347 A | 3/2000 | Cupferman et al. |
| 6,045,817 A | 4/2000 | Ananthapadmanabhan et al. |
| 6,107,261 A | 8/2000 | Taylor et al. |
| 6,110,908 A | 8/2000 | Guthery |
| 6,136,771 A | 10/2000 | Taylor et al. |
| 6,183,766 B1 | 2/2001 | Sine et al. |
| 6,187,327 B1 | 2/2001 | Stack |
| 6,204,230 B1 | 3/2001 | Taylor et al. |
| 6,211,243 B1 | 4/2001 | Johnson |
| 6,248,343 B1 * | 6/2001 | Jampani et al. |
| 6,287,577 B1 | 9/2001 | Beerse |
| 6,287,583 B1 | 9/2001 | Warren et al. |
| 6,294,186 B1 | 9/2001 | Beerse et al. |
| 6,319,958 B1 | 11/2001 | Johnson et al. |
| 6,321,750 B1 | 11/2001 | Kelly |
| 6,323,171 B1 | 11/2001 | Fonsny et al. |
| 6,344,218 B1 | 2/2002 | Dodd |
| 6,352,701 B1 | 3/2002 | Scholz et al. |
| 6,376,522 B1 * | 4/2002 | Holzl et al. |
| 6,387,357 B1 | 5/2002 | Chopra et al. |
| 6,403,067 B1 | 6/2002 | Schamper et al. |
| 6,403,071 B1 | 6/2002 | Scavone et al. |
| 6,414,032 B1 | 7/2002 | Johnson |
| 6,420,431 B1 | 7/2002 | Johnson |
| 6,426,062 B1 | 7/2002 | Chopra et al. |
| 6,485,716 B1 | 11/2002 | Fei et al. |
| 6,511,657 B2 | 1/2003 | Avendano et al. |
| 6,582,711 B1 | 6/2003 | Asmus et al. |
| 6,613,312 B2 | 9/2003 | Rizvi et al. |
| 6,682,749 B1 | 1/2004 | Potechin et al. |
| 6,723,689 B1 | 4/2004 | Hoang et al. |
| 6,846,846 B2 * | 1/2005 | Modak et al. |
| 7,435,429 B2 * | 10/2008 | Modak et al. |
| 7,563,461 B2 | 7/2009 | Modak et al. |
| 2002/0022660 A1 | 2/2002 | Jampani et al. |
| 2002/0098159 A1 | 7/2002 | Wei et al. |
| 2002/0165130 A1 | 11/2002 | Johnson et al. |
| 2003/0134780 A1 | 7/2003 | Patt |
| 2003/0152644 A1 | 8/2003 | Modak et al. |
| 2003/0157138 A1 | 8/2003 | Eini et al. |
| 2003/0211066 A1 | 11/2003 | Scholz |
| 2004/0102429 A1 | 5/2004 | Modak et al. |
| 2004/0208908 A1 | 10/2004 | Modak et al. |
| 2004/0253275 A1 | 12/2004 | Eini et al. |
| 2005/0019431 A1 | 1/2005 | Modak et al. |
| 2005/0048139 A1 | 3/2005 | Modak et al. |
| 2005/0238602 A1 | 10/2005 | Modak et al. |
| 2005/0281762 A1 | 12/2005 | Modak et al. |
| 2006/0141017 A1 | 6/2006 | King et al. |

FOREIGN PATENT DOCUMENTS

| | | |
|---|---|---|
| DE | 4240674 | 3/1994 |
| DE | 195 23 320 | 1/1997 |
| DE | 19523320 | 1/1997 |
| EP | 0041448 | 12/1981 |
| EP | 304802 A * | 3/1989 |
| EP | 402078 | 12/1990 |
| EP | 0521455 | 1/1993 |
| EP | 0604848 | 7/1994 |
| EP | 0 674 896 | 10/1995 |
| EP | 0674896 | 10/1995 |
| EP | 0694310 | 1/1996 |
| EP | 0313302 | 4/1998 |
| EP | 1 001 012 | 5/2000 |
| EP | 1001012 | 5/2000 |
| FR | 2729050 | 7/1996 |
| JP | 10328284 A * | 12/1998 |
| RU | 2166309 | 5/2001 |
| SU | 833240 | 5/1981 |
| WO | WO8400111 | 1/1984 |
| WO | WO8704350 | 7/1987 |
| WO | WO 88/00795 | 2/1988 |
| WO | WO8800795 | 2/1988 |
| WO | WO8803799 | 6/1988 |
| WO | WO8905645 | 6/1989 |
| WO | WO9307903 | 4/1993 |
| WO | WO9318745 | 9/1993 |
| WO | WO9318852 | 9/1993 |
| WO | WO9415461 | 7/1994 |
| WO | WO 94/18939 | 9/1994 |
| WO | WO9526134 | 10/1995 |
| WO | WO 98/24426 | 6/1998 |
| WO | WO9824426 | 6/1998 |
| WO | WO 9851275 A1 * | 11/1998 |
| WO | WO9903463 | 1/1999 |
| WO | WO9938505 | 5/1999 |
| WO | WO99/38505 | 8/1999 |
| WO | WO9938505 | 8/1999 |
| WO | WO 99/51192 | 10/1999 |
| WO | WO 99/60852 | 12/1999 |
| WO | WO9960852 | 12/1999 |
| WO | WO9963816 | 12/1999 |
| WO | WO0037042 | 6/2000 |
| WO | WO 01/41573 | 6/2001 |
| WO | WO0141573 | 6/2001 |
| WO | WO03003896 | 1/2003 |
| WO | WO 03/034994 | 5/2003 |
| WO | WO03034994 | 5/2003 |
| WO | WO 03/066001 | 8/2003 |
| WO | WO03/066001 | 8/2003 |
| WO | WO 03/083028 | 10/2003 |
| WO | WO03083028 | 10/2003 |
| WO | WO2004014416 | 2/2004 |
| WO | WO2006099359 | 9/2006 |
| WO | WO2007069214 | 6/2007 |

OTHER PUBLICATIONS

Modak et al., 2005, A topical cream containing a zinc gel (allergy guard) as a prophylactic against latex glove related contact dermatitis. Dermatitis. 16(1) 22-7.

de Abreu Gonzaga et al., Composition and antibacterial activity of the essential oils from *Zanthoxylum rhoifolium*. 2003, Planta Med. 69(8):773-775.

Bezic et al., 2003, Composition and antimicrobial activity of *Achillea clavennae* L. essential oil. Phytother. Res. 17(9):1037-1040.

Brehm-Stecher et al. 2003, Sensitization of *Staphylococcus aureus* and *Escherichia coli* to antibiotics by the sesquiterpenoids nerolidol, farnesol, bisabolol, and apritone. Antimicrobial Agents and Chemotherapy, 47(10):3357-3360.

Cimiotti et al., 2003, "Adverse reactions associated with an alcohol-based hand antiseptic among nurses in a neonatal intensive care unit." Am. J. Infect. Control 31:43-48.

Garcia et al., 2003, Virucidal activity of essential oils from aromatic plants of San Luis, Argentina. Phytother. Res. 17(9):1073-1075.

Goren et al., 2003, Analysis of essential oil of *Coridothymus capitatus* (L.) and its antibacterial and antifungal activity. Z. Naturforsch. 58(9-10):687-690.

Hajhashemi et al., 2003, Anti-inflammatory and analgesic properties of the leaf extracts and essential oil of *Lavandula angustifolia* Mill. J. Ethnopharmacol. 89(1):67-71.

Minami et al., 2003, The inhibitory effect of essential oils on herpes simplex virus type-1 replication in vitro. Microbial Immunol. 47(a):681-684.

Paranagama et al., 2003, Fungicidal and anti-aflatoxigenic effects of the essential oil of *Cymbopogon citratus* (DC.) Stapf. (lemongrass) against *Aspergillus flavus* Link. isolated from stored rice. Lett. Appl. Microbiol. 37(1):86-90.

Schuhmacher et al., 2003, Virucidal effect of peppermint oil on the enveloped viruses herpes simplex virus type 1 and type 2 in vitro. Phytomedicine 10:504-510.

Shin, 2003, Anti-*Aspergillus* activities of plant essential oils and their combination effects with ketoconazole or amphotericin B. Arch. Pharm. Res. 26(5):389-393.

Silva et al., 2003, Analgesic and anti-inflammatory effects of essential oils of *Eucalyptus*. J. Ethnopharmacol. 89(2-3);277-283.

Valero and Salmera, 2003, Antibacterial activity of 11 essential oils against *Bacillus cereus* in tyndallized carrot broth. Int. J. Food Microbiol. 85(1-2): 73-81.

Velluti et al., 2003, Inhibitory effect of cinnamon, clove, lemongrass, oregano and palmarose essential oils on growth and fumonisin B1 production by *Fusarium proliferatum* in maize grain. Int. J. Food Microbiol. 89:145-154.

Bleasel et al., 2002, "Allergic contact dermatitis following exposure to essential oils" Australian Journal of Dermatology 43:211-213.

Vilaplana et al., 2002, "Contact dermatitis from the essential oil of tangerine in fragrances" Contact Dermatitis 46:108.

Larsen et al., 2001 "Fragrance contact dermatitis: a worldwide multicenter investigation (Part II)" Contact Dermatitis 44:344-346.

Nair, 2001, "Final report on the safety assessment of *Mentha piperita* (Peppermint) oil, *Mentha piperita* (Peppermint) Leaf extract, *Mentha piperita* (Peppermint) leaf and *Mentha piperita* (Peppermint) water" International Journal of Toxicology 20 (Suppl 3):61-73.

Wohrl, 2001 "The significance of fragrance mix, balsam of Peru, colophony and propolis as screening tools in the detection of fragrance allergy" British Journal of Dermatology 145(2):268-273.

Sugiura., 2000, "Results of patch testing with lavender oils in Japan" Contact Dermatitis 43:157-160.

De Groot et al., 1997, "Adverse reactions to fragrances: a clinical review." Contact Dermatitis 36:57-86.

Modak et al., A Topical Zinc Gluconate Gel Composition for the Prevention of latex/Starch Glove Related Allergic Reactions: Pilot Study in Volunteers. In: Programs and Abstracts of the 37th Interscience Conference on Antimicrobial Agents and Chemotherapy, Toronto: 1997; American Society for Microbiology Washington DC. Abstract J -52.

Goodman and Gilman's The Pharmacological Basis of Therapeutics (Goodman Gilman A, Rall TW, Nies AS, Taylor P, ed. (Pergamon Press; Elmsford, N.Y.: 1990).

Bush et al., 1986, "Pig skin as test substrate for evaluating topical antimicrobial activity" J Clin Microbiol 24:343-348.

Meyer et al., 1978, "The skin of domestic mammals as a model for the human skin, with special reference to the domestic pig." Curr. Problem Dematol 7:39-52.

Rosenthal, S.L., Effect of Medicaments on the Motility of the Oral Flora with Special Reference to the Treatment of Vincent's Infection. II. Journal of Dental Research. 1943, vol. 22, pp. 491-494.

U.S. Appl. No. 10/622,272, filed Jul. 17, 2003.
U.S. Appl. No. 11/031,258, filed Jan. 7, 2005.
U.S. Appl. No. 11/143,012, filed Jun. 2, 2005.
U.S. Appl. No. 11/327,677, filed Jan. 6, 2006.
U.S. Appl. No. 11/446,347, filed Jun. 2, 2006.
U.S. Appl. No. 10/892,034, filed Jul. 15, 2004.
U.S. Appl. No. 08/492,080, filed Jun. 28, 1995.
U.S. Appl. No. 08/760,054, filed Dec. 4, 1996.
U.S. Appl. No. 08/871,071, filed Jun. 9, 1997.
U.S. Appl. No. 09/387,550, filed Aug. 31, 1999.
U.S. Appl. No. 10/047,631, filed Oct. 23, 2001.
U.S. Appl. No. 10/785,207, filed Feb. 24, 2004.
U.S. Appl. No. 10/786,681, filed Feb. 25, 2004.
U.S. Appl. No. 08/218,666, filed Mar. 28, 1994.
U.S. Appl. No. 10/622,272, Apr. 13, 2007 Non-Final Office Action.
U.S. Appl. No. 10/622,272, Oct. 15, 2007 Response to Non-Final Office Action.
U.S. Appl. No. 10/622,272, Jan. 30, 2008 Non-Final Office Action.
U.S. Appl. No. 10/622,272, Apr. 28, 2008 Response to Non-Final Office Action.
U.S. Appl. No. 10/622,272, Jul. 4, 2008 Final Office Action.
U.S. Appl. No. 10/622,272, Nov. 21, 2008 Response to Final Office Action.
U.S. Appl. No. 10/622,272, Jan. 22, 2009 Non-Final Office Action.
U.S. Appl. No. 10/622,272, Apr. 22, 2009 Response to Non-Final Office Action.
U.S. Appl. No. 10/622,272, Jul. 2, 2009 Final Office Action.
U.S. Appl. No. 10/622,272, Sep. 29, 2009 Response to Final Office Action.
U.S. Appl. No. 10/622,272, Dec. 21, 2009 Non-Final Office Action.
U.S. Appl. No. 10/785,207, Nov. 19, 2007 Non-Final Office Action.
U.S. Appl. No. 10/785,207, Feb. 19, 2008 Response to Non-Final Office Action.
U.S. Appl. No. 10/785,207, May 14, 2008 Final Office Action.
U.S. Appl. No. 10/785,207, Aug. 13, 2008 Response to Final Office Action.
U.S. Appl. No. 10/785,207, Sep. 22, 2008 Non-Final Office Action.
U.S. Appl. No. 10/785,207, Dec. 18, 2008 Response to Non-Final Office Action.
U.S. Appl. No. 10/785,207, Mar. 5, 2009 Final Office Action.
U.S. Appl. No. 10/785,207, May 28, 2009 Response to Final Office Action.
U.S. Appl. No. 10/785,207, Aug. 11, 2009 Non-Final Office Action.
U.S. Appl. No. 10/785,207, Nov. 2, 2009 Response to Non-Final Office Action.
U.S. Appl. No. 10/786,681, May 21, 2007 Non-Final Office Action.
U.S. Appl. No. 10/786,681, Sep. 6, 2007 Response to Non-Final Office Action.
U.S. Appl. No. 10/786,681, Nov. 21, 2007 Final Office Action.
U.S. Appl. No. 10/786,681, Feb. 21, 2008 Response to Final Office Action.
U.S. Appl. No. 10/786,681, Jul. 7, 2008 Non-Final Office Action.
U.S. Appl. No. 10/786,681, Oct. 2, 2008 Response to Non-Final Office Action.
U.S. Appl. No. 10/786,681, Dec. 23, 2008 Final Office Action.
U.S. Appl. No. 10/786,681, Mar. 23, 2009 Response to Final Office Action.
U.S. Appl. No. 10/786,681, May 27, 2009 Non-Final Office Action.
U.S. Appl. No. 10/786,681, Aug. 27, 2009 Response to Non-Final Office Action.
U.S. Appl. No. 10/786,681, Nov. 24, 2009 Final Office Action.
U.S. Appl. No. 10/892,034, Jan. 29, 2008 Non-Final Office Action.
U.S. Appl. No. 10/892,034, Jun. 17, 2008 Response to Non-Final Office Action.
U.S. Appl. No. 10/892,034, Aug. 27, 2008 Final Office Action.
U.S. Appl. No. 10/892,034, Jan. 27, 2009 Response to Final Office Action.
U.S. Appl. No. 10/892,034, Apr. 8, 2009 Non-final Office Action.
U.S. Appl. No. 10/892,034, Jul. 2, 2009 Response to Non-Final Office Action.
U.S. Appl. No. 10/892,034, Oct. 9, 2009 Final Office Action.
U.S. Appl. No. 11/327,677, Jun. 1, 2009 Non-Final Office Action.
U.S. Appl. No. 11/327,677, Aug. 27, 2009 Response to Non-final Office Action.
U.S. Appl. No. 11/327,677, Nov. 2, 2009 Notice of Allowance.
U.S. Appl. No. 11/143,012, Oct. 31, 2008 Non-Final Office Action.
U.S. Appl. No. 11/143,012, Jan. 16, 2009 Response to Non-Final Office Action.
U.S. Appl. No. 11/143,012, Mar. 24, 2009 Notice of Allowance.
U.S. Appl. No. 11/031,258, Jun. 6, 2007 Non-Final Office Action.
U.S. Appl. No. 11/031,258, Aug. 22, 2007 Response to Non-Final Office Action.
U.S. Appl. No. 11/031,258, Dec. 6, 2007 Notice of Allowance.
U.S. Appl. No. 10/047,631, Nov. 14, 2003 Non-Final Office Action.
U.S. Appl. No. 10/047,631, Apr. 16, 2004 Response to Non-Final Office Action.
U.S. Appl. No. 10/047,631, Jul. 12, 2004 Notice of Allowance.
U.S. Appl. No. 11/446,347, Sep. 1, 2009 Non-Final Office Action.
U.S. Appl. No. 08/492,080, Sep. 13, 1996 Non-Final Office Action.

U.S. Appl. No. 08/492,080, Jan. 13, 1997 Response to Non-Final Office Action.
U.S. Appl. No. 08/492,080, Apr. 19, 1997 Final Office Action.
U.S. Appl. No. 08/492,080, Jul. 9, 1997 Response to Final Office Action.
U.S. Appl. No. 08/492,080, Aug. 5, 1997 Examiner Interview Summary Record.
U.S. Appl. No. 08/492,080, Aug. 6, 1997 Notice of Allowance.
U.S. Appl. No. 08/760,054, Mar. 28, 1997 Non-Final Office Action.
U.S. Appl. No. 08/760,054, Jul. 28, 1997 Response to Non-Final Office Action.
U.S. Appl. No. 08/760,054, Nov. 19, 1997 Final Office Action.
U.S. Appl. No. 08/760,054, Apr. 17, 1998 Notice of Appeal Filed.
U.S. Appl. No. 08/760,054, Apr. 17, 1998 Amendment/Argument after Notice of Appeal.
U.S. Appl. No. 08/760,054, May 15, 1998 Advisory Action.
U.S. Appl. No. 08/760,054, Aug. 17, 1998 Express Abandonment.
U.S. Appl. No. 08/760,054, Aug. 17, 1998 Continuing Prosecution Application—Continuation (ACPA).
U.S. Appl. No. 08/760,054, Nov. 24, 1998 Non-Final Office Action.
U.S. Appl. No. 08/760,054, Mar. 17, 1999 Response to Non-Final Office Action.
U.S. Appl. No. 08/760,054, Jun. 18, 1999 Examiner's Amendment.
U.S. Appl. No. 08/760,054, Jun. 21, 1999 Notice of Allowance.
U.S. Appl. No. 08/871,071, May 8, 1998 Non-Final Office Action.
U.S. Appl. No. 08/871,071, Nov. 9, 1998 Response to Non-Final Office Action.
U.S. Appl. No. 08/871,071, Dec. 9, 1998 Terminal Disclaimer Approved.
U.S. Appl. No. 08/871,071, Dec. 16, 1998 Non-Final Office Action.
U.S. Appl. No. 08/871,071, Mar. 19, 1999 Response to Non-Final Office Action.
U.S. Appl. No. 08/871,071, Apr. 16, 1999 Notice of Allowance.
U.S. Appl. No. 09/387,550, Nov. 9, 1999 Notice of Allowance.
U.S. Appl. No. 09/387,550, Nov. 4, 2004 Certificate of Correction.
U.S. Appl. No. 09/387,550, Nov. 22, 2005 Certificate of Correction.
U.S. Appl. No. 08/218,666, Mar. 3, 1995 Non-Final Office Action.
U.S. Appl. No. 08/218,666, Sep. 7, 1995 Response to Non-Final Office Action.
U.S. Appl. No. 08/218,666, Dec. 18, 1995 Final Office Action.
3M Avagard Surgical and Healthcare Personnel Hand Antiseptic with Moisturizers news release, 3M Company, Jun. 11, 2001.
3M Avagard Surgical and Healthcare Personnel Hand Antiseptic with Moisturizers product description, 3M Company, 2001.
A-Z of exhibitors; at Central European Coatings Show, PPC1. Polymers Paint Colour Journal, No. 4433, vol. 190, p. 42, Oct. 1, 2000.
Beilfuss, "A multifunctional ingredient for deodorants," SOFW Journal, 1998, vol. 124, p. 360, 362-364, 366.
"Drug Information for the Health Care Professional," vol. 1A, USP-DI, 1989, Ninth Edition, pp. 792-793, Banta Company, VIR.
Fitzgerald, K.A., Davies, A., and Russel, A.D., "Mechanism of Action of Chlorhexidine Diacitate and Phenoxyethanol Singly and in Combination Against Gram-negative Bacteria," 215 Mibrobio 70:215-229 (1992).
"Fraicheur de Peau Fresh Skin Body Mist," International Product Alert, No. 9, vol. 14, May 5, 1997.
Happi, Household & Personal Products Industry: New ingredients galore at SCC supplier's day, Chemical Business Newsbase, Aug. 1, 2000.
Heard, D.D., and Ashworth, R.W., "The Colloidal Properties of Chlorhexidine and its Interaction with Some Macromolecules," J. Pharm. Pharmac. 20:505-12, 1968.
Lansdown, "Interspecies variations in response to topical application of selected zinc compounds," Food Chern Toxicol. Jan. 1991;29(I):57-64.
Lawrence, J.C. et al., "Evaluation of Phenoxeotol—Chlorhexidine Cream as a Prophylactic Antibacterial Agent in Burns," The Lancet, pp. 1037-1040, May 8, 1992.
Manufacturing Chemist: Japan approve Schulke & Mayr's Sensiva SC 50, Chemical Business Newsbase, Jul. 14, 2000.
Modak S. et al., "Rapid Inactivation of Infections Pathogess by Chlorhexidine Coated Gloves," Infection Control and Hospital Epidemiology, 13:463-471, (1992).
Molnycke Healthcare "Hibiclens Antiseptic/Antimicrobial Skin Cleanser" Nov. 10, 2006.
Parfums, Cosmetiques, Aromes: Japan approves sale of new cosmetics ingredient, Chemical Business Newsbase, Jan. 16, 2001.
Physicians Desk Reference—39th Edition, 1985, p. 1858, Lotrisone.
Physicians Desk Reference—39th Edition, 1985, pp. 2037-2038, chlorhexidine.
Physicians Desk Reference—40th Edition, 1986, pp. 1781-1782, chlorhexidine.
Pfizer "Purell Instant Hand Sanitizer, Product Description" Nov. 10, 2006.
Prevacare: Antimicrobial Hand Gel product description, Johnson & Johnson, Advanced Wound Care, 2001.
Prevcare: Total solution skin care spray product description, Johnson & Johnson, Advanced Wound Care, 2001.
Robinson, K. "Heat beating technology; deodorant market," Soap Perfumery and Cosmetics, v. 69 No. 7 p. 34, Jul. 1996.
Rubbo et al., A Review of Sterilization and Disinfection, Year Book Medical Publishers, Chicago, 161-162 (1965).
S &M in Japan—Schulke & Mayr's Sensiva SC 50 deodorant active ingredient received approval for use in the Japanese market, SPC Asia No. 21, p. 35, May 2000.
Schmolka, I.R., "The Synergistic Effects of Nonionic Surfactants Upon Cationic Germicidal Agents," J. Soc. Cosmet. Chem., 24:577-592, 1973.
Schwarzkopf cares, European Cosmetic Markets, No. 5, vol. 13, May 1, 1996.
Schwarzkopf: Moving into a new area, European Cosmetic Markets, No. 9, Sep. 1, 1996.
Sensiva SC 50 product description from manufacturer website (www.schuelkemayr.com), Schulke & Mayr, manufacturer, printed Apr. 4, 2001.
SPC, Soap Perfumery and Cosmetics: New for deodorants: Sensiva SC 50, Chemical Business Newsbase, Aug. 12, 1999.
Vichy launches oil-free moisturizer, Chemist & Druggist, p. 792, Jun. 8, 1996.
Woodruff,l. "Mixed feelings," Soap Perfumery & Cosmetics, No. 9, vol. 73, p. 39, Sep. 1, 2000.
Ebner et al. Am. J. Clin. Dermatol., vol. 3, No. 6, pp. 427-433.
U.S. Appl. No. 10/892,034, May 17, 2010 Non-Final Office Action.
U.S. Appl. No. 11/446,347, Jun. 2, 2010 Response to Amendment after Notice of Allowance.
Aiko Tanaka et al. "Effect of Various Types of Disinfectants on Skin Physiological Function." J. Nursing Science. Toyama Medical and Pharmaceutical University. 1999, vol. 2 pp. 49-58.
U.S. Appl. No. 12/715,026, filed Mar. 1, 2010.
U.S. Appl. No. 10/785,207, Jan. 29, 2010 Supplemental Response to Office Action.
U.S. Appl. No. 10/622,272, Apr. 21, 2010 Response to Non-Final Office Action.
U.S. Appl. No. 10/785,207, May 13, 2010 Final Office Action.
U.S. Appl. No. 10/786,681, Feb. 24, 2010 Response to Final Office Action.
U.S. Appl. No. 10/786,681, Mar. 30, 2010 Non-Final Office Action.
U.S. Appl. No. 10/892,034, Feb. 8, 2010 Response to Final Office Action.
U.S. Appl. No. 10/892,034, May 17, 2010 Response to Final Office Action.
U.S. Appl. No. 11/327,677, Feb. 23, 2010 Notice of Allowance.
U.S. Appl. No. 11/327,677, Apr. 16, 2010 Amendment after Notice of Allowance.
U.S. Appl. No. 11/327,677, May 10, 2010 Notice of Allowance.
U.S. Appl. No. 11/446,347, Feb. 26, 2010 Response to Non-Final Office Action.
U.S. Appl. No. 11/446,347, Mar. 15, 2010 Notice of Allowance.
U.S. Appl. No. 11/446,347, May 18, 2010 Amendment after Notice of Allowance.
U.S. Appl. No. 11/446,347, May 18, 2010 Response to Amendment after Notice of Allowance.
U.S. Appl. No. 10/622,272, dated Jul. 22, 2010 Non-Final Office Action.

* cited by examiner

ANTIMICROBIAL COMPOSITIONS CONTAINING SYNERGISTIC COMBINATIONS OF QUATERNARY AMMONIUM COMPOUNDS AND ESSENTIAL OILS AND/OR CONSTITUENTS THEREOF

1. CROSS REFERENCE TO RELATED APPLICATIONS

The present application claims the benefit of U.S. Provisional Application Ser. Nos. 60/488,349, and 60/530,864, filed Jul. 17, 2003, and Dec. 18, 2003, respectively, each of which are incorporated herein by reference in their entireties.

2. INTRODUCTION

The present invention relates to compositions comprising combinations of quaternary ammonium compounds and essential oils and/or individual constituents thereof, and methods of using such compositions. It is based, at least in part, on the discovery that such combinations exhibit synergistically enhanced antimicrobial effects.

3. BACKGROUND OF THE INVENTION

Essential oils are volatile oils obtained from plant or animal sources and are composed of complex mixtures of several constituents, such as monoterpenes and sesquiterpene hydrocarbons, monoterpene and sesquiterpene alcohols, esters, ethers, aldehydes, ketones, oxides and the like. These essential oils and their isolated constituents are frequently utilized as fragrance and flavor agents, and have been widely used in folk medicine for wound healing properties.

Scientific research has corroborated the beneficial effects of essential oils. Essential oils of eucalyptus have been found to "possess central and peripheral analgesic effects as well as neutrophil-dependent and independent anti-inflammatory activities" (Silva et al., 2003, J. Ethnopharmacol. 89(2-3); 277-283), and similar activity has been observed in essential oils from *Lavendula angustifolia* Mill. (Hajhashemi et al., 2003, J. Ethnopharmacol. 89(1):67-71). Essential oils have been demonstrated to exhibit antibacterial (Bezic et al., 2003, Phytother. Res. 17(9:1037-1040; Goren et al., 2003, Z. Naturforsch. 58(9-10):687-690; de Abreu Gonzaga et al., 2003, Planta Med. 69(8):773-775; Valero and Salmera, 2003, Int. J. Food Microbiol. 85(1-2): 73-81) and antifungal (Paranagama et al., 2003, Lett. Appl. Microbiol. 37(1):86-90; Shin, 2003, Arch. Pharm. Res. 26(5):389-393; Velluti et al., 2003, Int. J. Food Microbiol. 89:145-154) activities. Virucidal activity of essential oils has also been observed, including direct virucidal effects against Herpes simplex viruses types 1 and 2 (Garcia et al., Phytother. Res. 17(9):1073-1075; Minami et al., 2003, Microbial Immunol. 47(a):681-684; Schuhmacher et al., 2003, Phytomedicine 10:504-510).

Quaternary ammonium compounds ("QAC") are a group of ammonium salts in which organic radicals have been substituted for all four hydrogens of the original ammonium cation. They have a central nitrogen atom which is joined to four organic radicals and one acid radical. QACs have a tendency to distribute to the interface of two phases (liquid-liquid or solid-liquid) to introduce continuity between the two different phases. QACs are known to have potent antimicrobial activity, capable of disrupting bacterial cell processes. QACs have been used as antiseptics, disinfectants, preservatives, biocides, etc.

Johnson et al. (U.S. Pat. No. 6,319,958 and US20020165130) relates to the use of sesquiterpenoids to promote uptake of exogenous antimicrobial compounds. Similarly, a related article discloses the use of sesquiterpenoids, such as nerolidol, farnesol, bisabolol and apritone, in enhancing bacterial permeability and susceptibility to exogenous antimicrobial compounds, suggesting that sesquiterpenoids have a non-specific and general effect (Brehm-Stecher et al. 2003, Antimicrobial Agents and Chemotherapy, 47(10): 3357-3360). In particular, Brehm-Stecher et al. report that nerolidol, farnesol, bisabolol and apritone enhanced the susceptibility of *S. aureus* to the antibiotics erythromycin, gentamicin, vancomycin, ciproflaxin, clindamycin, and tetracycline. In addition, Brehm-Stecher et al. does not disclose the use of QACs as antimicrobial agents.

There is a continuing desire for an antimicrobial composition that is non-irritating, safe, and effective for repeated use in various professional and non-professional settings.

4. SUMMARY OF THE INVENTION

The present invention relates to antimicrobial compositions comprising combinations of quaternary ammonium compounds and essential oils and/or individual constituents thereof. Such combinations may be comprised in lotions, gels, creams, soaps, etc. for application to skin or mucous membranes. The invention is based, at least in part, on the observation that synergistic antimicrobial effects are achieved with combinations of essential oils and/or individual constituents thereof and low concentrations of quaternary ammonium compounds.

5. DETAILED DESCRIPTION OF THE INVENTION

The present invention relates to compositions and methods for their use, wherein the antimicrobial activities of gels, creams, ointments, lotions or soaps is enhanced by the inclusion of synergistic amounts of quaternary ammonium compounds and essential oils and/or one or more individual constituent(s) thereof. The formulations of the instant invention comprise a synergistically effective amount of at least one quaternary ammonium compound and at least one essential oil and/or individual constituent(s) thereof.

The use of the terms, "synergistic" and "synergistically effective," are used in the present invention to mean a biological effect created from the application of two or more agents to produce a biological effect that is greater than the sum of the biological effects produced by the application of the individual agents.

Examples of quaternary ammonium compounds suitable for use in the instant invention include, but are not limited to, benzalkonium chloride ("BZK"), benzethonium chloride ("BZT"), other benzalkonium or benzethonium halides, including, but not limited to, benzalkonium or benzethonium bromide or fluoride, cetyl pyridinium chloride, alkylamidopropalkonium chloride, behenalkonium chloride, behentrimonium methosulphate, behenamidopropylethyldimonium ethosulphate, stearalkonium chloride, olealkonium chloride, cetrimonium chloride, dequalinium chloride, N-myristyl-N-methyl-morpholinium methyl sulfate, poly[N-[3-(dimethylammonio)propyl]-N'-[3-(ethyleneoxyethelene-dimethylammoinio)propyl]urea dichloride], alpha-4-[1-tris (2-hydroxyethyl)ammonium chloride-2-butenyl]-omega-tris (2-hydroxyethyl)ammonium chloride, poly[oxyethylene (dimethyliminio)ethylene(dimethyliminio)-ethylene dichloride].

The concentrations of quaternary ammonium compound may be between about 0.01 and 0.5 percent; preferably the quaternary ammonium compound is benzethonium chloride or benzalkonium chloride at a concentration between 0.05 and 0.3 percent, more preferably between 0.1 and 0.2 percent. These percentages, and other percentages herein, unless specified otherwise, are weight/weight.

Essential oils ("EOs"), as defined herein, are volatile oils obtained from plant or animal sources, or their synthetic equivalents, and are composed of complex mixtures of several constituents as monoterpenes and sesquiterpene hydrocarbons, monoterpene and sesquiterpene alcohols, esters, ethers, aldehydes, ketones, oxides and the like. Examples of EOs include, but are not limited to, bergamot oil, clary sage oil, ylang-ylang oil, neroli oil, sandalwood oil, frankincense oil, ginger oil, peppermint oil, lavender oil, jasmine absolute, geranium oil bourbon, spearmint oil, clove oil, patchouli oil, rosemary oil, rosewood oil, sandalwood oil, tea tree oil, vanilla oil, lemongrass oil, cedarwood oil, balsam oils, tangerine oil, Hinoki oil, Hiba oil, ginko oil, eucalyptus oil, lemon oil, orange oil, and sweet orange oil.

Individual constituents ("ICs") of essential oils may be isolated from the oil (natural) or entirely or partially synthetic, and include, but are not limited to, 1-citronellol, α-amylcinnamaldehyde, lyral, geraniol, farnesol, hydroxycitronellal, isoeugenol, eugenol, eucalyptol, linalool, citral, thymol, limonene and menthol.

Further examples of ICs include sesquiterpenoid compounds, which may be the active compounds in the essential oils. Sesquiterpenoid compounds, containing 15 carbons, are formed biosynthetically from three 5-carbon isoprene units. Sesquiterpenoid compounds include, but are not limited to, farnesol, nerolidol, bisabolol, apritone, chamazulene, santalol, zingiberol, carotol, and caryophyllen.

Mixtures of one or more EO, one or more IC, and one or more EO as well as one or more IC, are encompassed by the present invention.

The concentrations of EOs and ICs may be between about 0.01 and 10 percent; preferably between 0.05 and 1.0 percent or between 0.05 and 0.5 percent, and more preferably between 0.2 and 0.5 percent. In preferred embodiments, the EO is lemon oil and/or the IC is farnesol.

In certain specific, non-limiting embodiments, the present invention provides for formulations, including but not limited to gels, creams, lotions or ointments further comprising an amount of zinc that inhibits irritation of the skin or mucosa to which the formulation is applied. Zinc may be added counteract the irritating effects of essential oils. The use of zinc in topical compositions is known in the art and disclosed in the following patents: U.S. Pat. Nos. 5,708,023, 5,965,610, 5,985,918 and 6,037,386.

In a preferred embodiment of the invention, low concentrations of two or more water-soluble salts of zinc are used. The term "low concentration" means percentages of free zinc ions ($Zn^{2+}$) in the gel or cream at less than 0.5% on a weight to weight (w/w) basis. Suitable zinc salts for use in these compositions include zinc acetate (molar solubility in water of 1.64 moles/l), zinc butyrate (molar solubility in water of 0.4 moles/l), zinc citrate (molar solubility in water of <0.1 moles/l), zinc gluconate (molar solubility in water of 0.28 moles/l), zinc glycerate (moderately water soluble), zinc glycolate (moderately water soluble), zinc formate (molar solubility in water of 0.33 moles/l), zinc lactate (molar solubility in water of 0.17 moles/l), zinc picolinate (moderately water soluble), zinc proprionate (molar solubility in water of 1.51 moles/l), zinc salicylate (low water solubility), zinc tartrate (moderately water soluble) and zinc undecylenate (moderately water soluble). In particularly preferred embodiments, the zinc salts comprise a combination of effective amounts of two or more of the following: zinc acetate (0.05-2.0%), zinc citrate (0.05-2.0%), zinc gluconate (0.05-2.0%) and zinc lactate (0.05-2.0%). In preferred embodiments, the zinc salts are 0.2-0.6% zinc gluconate, 0.1-0.3% zinc acetate and 0.1-0.3% zinc lactate. In particularly preferred embodiments, the zinc salts are 0.3% zinc gluconate, 0.1% zinc acetate, and 0.1% zinc lactate, or 0.2% zinc zinc lactate and 0.2% zinc gluconate. Additional compositions that may comprise the synergistic combinations of the invention are described in International Patent Application No. PCT/US03/03896, published on Aug. 14, 2003, as WO03/066001, incorporated by reference herein in its entirety.

The gels, ointments, lotions or creams of the invention may be applied topically to the skin or to the various mucous membranes of the body, including but not limited to those of the oral, nasal, vaginal or rectal cavities.

In preferred embodiments, the gel, lotion, ointment or cream may comprise a mixture of water, a gelling agent, a thickening agent, a hydrophilic or hydrophobic polymer, an emulsifying agent, an emollient, and/or alcohol, such as ethanol. In preferred embodiments, the presently claimed compositions comprise alcohol present at 10-90% w/w, water present at 15-70% w/w, thickeners and/or gelling agents present at 0.05-3.0% w/w, and emollients present at 0.1-3.0% w/w.

In preferred embodiments, if a thickener is present, it is not a polyacrylic acid-based thickener, such as but not limited to, carbomer, carbopol, or ultrez, as polyacrylic acid-based thickeners have been found to be incompatible with quaternary ammonium compounds. Without being bound by any particular theory, it is believed that anionic groups of such thickeners may interact with cationic groups of the quaternary ammonium compound. Preferably, if a gelling agent is used, it is not an anionic agent, but rather a non-ionic or cationic agent.

The compositions of the invention may optionally further include one or more additional antimicrobial agent such as, but not limited to, antiviral, antibacterial, or antifungal substances. Antimicrobial agents also include substances possessing any combination of virucidal or virustatic, bacteriocidal or bacteriostatic, or fingicidal or fungistatic properties. Antimicrobial agents are well known to those of ordinary skill in the art. Examples of antimicrobial agents include, but are not limited to, iodophors, iodine, benzoic acid, dehydroacetic acid, propionic acid, sorbic acid, methyl paraben, ethyl paraben, propyl paraben, butyl paraben, cetrimide, chlorhexidine (free base and/or salts), other biguanides, such as polyhexamethyl biguanide (PHMB) and chlorohexidine gluconate (CHG), chloroeresol, chlorxylenol, benzyl alcohol, bronopol, chlorbutanol, ethanol, phenoxyethanol, phenylethyl alcohol, 2,4-dichlorobenzyl alcohol, thiomersal, clindamycin, erythromycin, benzoyl peroxide, mupirocin, bacitracin, polymyxin B, neomycin, triclosan, parachlorometaxylene, foscarnet, miconazole, fluconazole, itriconazole, ketoconazole, and pharmaceutically acceptable salts thereof. These and further examples of antimicrobial agents useful in this invention can be found in such references as Goodman and Gilman's The Pharmacological Basis of Therapeutics (Goodman Gilman A, Rall T W, Nies A S, Taylor P, ed. (Pergamon Press; Elmsford, N.Y.: 1990)), the contents of which are hereby incorporated by reference.

In an embodiment, the compositions of the invention comprises a biguanide compound selected from the group consisting of chlorohexidine gluconate (CHG) and polyhexarnethyl biguanide (PHMB). Preferably, the biguande compound is present at a concentration of between 0.1 to 2.0% w/w.

Pharmaceutically acceptable chlorhexidine salts are well known to those of ordinary skill in the art and include, but are not limited to, chlorhexidine palmitate, chlorhexidine diphosphanilate, chlorhexidine digluconate ("CHG"), chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulphate, chlorhexidine sulphite, chlorhexidine thiosulphate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate.

In formulating compositions of this invention, it is contemplated that the formulations may further comprise ingredients which, while not having the activity of the above-named ingredients, will aid in the formulation and use of the composition as a whole. Examples of such ingredients are well-known to those of ordinary skill in the art of producing formulations for biological purposes. Examples of these ingredients include such substances as binders, emollients, preservatives (such as methyl paraben), lubricants, colorants, perfumes, and the like. Accordingly, when the surface contemplated is skin, the composition of this invention may contain ingredients which are added to known lotions or medicaments, which are physiologically acceptable to skin and which do not contain ingredients which will reverse or retard the action of the irritant-inactivating agent.

In certain non-limiting embodiments of the invention, the composition may be added to pre-existing formulations provided that the ingredients in those formulations do not prevent or retard the activity of the claimed composition. In a preferred embodiment, the claimed composition can be added to creams, ointments, gels or lotions which are commercially available. Examples of commercially available lubricants include, but are not limited to, those lubricants sold under the tradenames "KY JELLY," "ASTROGLIDE," and "PREVACARE." Examples of commercially available lotions include, but are not limited to, those lotions sold under the tradenames "SOFT-SENSE," "LOTION SOFT," "CUREL," and "KERI". SOFT-SENSE (Johnson & Son, Inc., Racine, Wis.) is known to contain purified water, glycerin USP, distearyldimonium chloride, petrolatum USP, isopropyl palmitate, 1-hexadecanol, tocopheryl acetate (vitamin E USP), dimethicone, titanium dioxide USP, methyl paraben, propyl paraben, sodium chloride, and fragrance. LOTION SOFT (Calgon Vestal, St. Louise, Mo.) is a nonionic moisturizing lotion which is known to contain mucopolysaccharide. CUREL (Bausch & Lomb Incorporated, Rochester, N.Y.) is known to contain deionized water, glycerin, quaternium-5, petrolatum, isopropyl palmitate, 1-hexadecanol, dimethicone, sodium chloride, fragrance, methyl paraben, and propyl paraben.

The claimed compositions may be used in anti-perspirants, aftershave lotions, hydroalcoholic skin disinfectants, and therapeutic creams, etc.

Certain preferred embodiments of the invention comprise, for example but not by way of limitation, one or more of the following: alcohol (10-90% w/w), which could include one or more of ethanol, n-propanol and iso-propanol; one or more zinc compound in an anti-irritant amount; one or more polymeric quaternary ammonium salts of hydroxyethyl cellulose reacted with trimethyl ammonium substituted epoxide (Polyquatemium), such as U-care polymer such as Ucare JR125, JR 400, JR 30M, LR 400, LR30M, or Ucare polymer LK; hydroxypropyl methyl cellulose such as the Methocel A,E,K, and 40 series products as Methocell K4MS, Methocel K100, Methocell 40-202, Methocel K15MS and others; one or more quaternary ammonium compound such as BZK or BZT; cetyltrimethyl ammonium chloride ("CTAC"); cetyl trimethyl ammonium bromide ("CTAB"); olealkonium chloride; stearalkonium chloride; Incroquat BA 85 (babassuamidopropalkonium chloride); dibehenyldimonium methosulfate; IncroquatBES-35 S (Behenamidopropylethyldimonium Ethosulfate and stearyl alcohol); Incroquat B-65C (Behenalkonium chloride and cetyl alcohol); Incroquat Behenyl TMS (Behentrimonium methosulfate and cetearyl alcohol); and one or more emollient, such as Procetyl 10 PPG-10 cetyl ether, Procetyl 50 PPG-50 cetyl ether, Promyristyl PM-3 PPG-3Myristyl ether, PPG-3 benzyl ether myristate (Crodamol STS of Croda), PEG 20 Almond Glycerides, Probutyl DB-10, Glucam P20, Glucam E-10, Glucam P-10, Glucam E-20, Glucam P-20 distearate, glycerin, propylene glycol, cetyl acetate and acetylated lanolin alcohol (Acetulan), hydroxylated milk glycerides (Cremerol HMG); a silicone fluid such as Dow Corning Silicone Fluid 245, 244, 246, 344, 345, 556; an essential oil such as lemon oil, citronella oil, sandalwood oil, lemongrass oil, patchouli oil, clove oil, thyme oil, geranium oil, basil oil; an individual constituent of an essential oil, such as farnesol, citronellol, linalool, eugenol, citral, thymol, eucalyptol, menthol; and a biguanide such as chlorhexidine gluconate or polyhexamethyl biguanide.

The invention provides for methods of using the foregoing compositions to achieve an antimicrobial effect comprising applying an effective amount of the composition to the surface. An antimicrobial effect significantly diminishes the risk of infection or progression of existing infection by one or more pathogenic infectious agent. The risk of infection need not be reduced to zero, but preferably is reduced by at least 10, 20, 30, 40, 50, 60, 70, 80, or 90 percent. Examples of infectious agents against which protection may be afforded include, but are not limited to, *Staphylococcus* species such as *Staphylococcus aureus* and *Staphylococcus epidermidis*, *Streptococcus* species such as *Streptococcus pneumoniae*, *Enterococcus* species, *Salmonella* species such as *Salmonella typh*, *Escherichia* species such as *Escherichia coli*, *Vibrio* species, *Neisseria* species, such as *Neisseria meningitidis* and *Neisseria gonnorhoea*, Human Immunodeficiency Virus (HIV), Human Papilloma Virus (HPV), Herpes Simplex Virus (HSV), *Chlamydia trachomatis*, *Trichomonas vaginalis*, and *Candida albicans*.

In an embodiment of the invention, the compositions of the present invention do not contain antibiotics, including, but are not limited to, tetracycline, ampicillin, rifampin, vancomycin, amphotericin B, nystatin, and bacitracin.

The following are specific, non-limiting examples of formulations of the present invention with and without zinc salts.

| FORMULATIONS WITHOUT ZINC SALTS | |
|---|---|
| General Formula Ingredients | Percent Range (w/w %) |
| Ethanol | 50-90 |
| Water | 15-35 |

| Ingredients | Percent (w/w) |
|---|---|
| U-care polymers | 01.-0.5 |
| Germall + | 0.15-0.3 |
| Quaternary ammonium compounds | 0.05-0.2 |
| Quaternary conditioners | 0.2-1.0 |
| Emollients | 0.3-1.0 |
| Phenoxyethanol (if present) | 0.5-1.0 |
| Silicone fluids | 0.2-1.0 |
| Essential oils/individual constituents | 0.3-1.0 |
| Biguanides (if present) | 0.05-2.0 |

Specific Formulas

| Ingredients | Percent (w/w) |
|---|---|
| (A) Alcohol surgical hand prep-1 | |
| Ethanol | 68 |
| Babassuamidopropalkonium Chloride | 0.5 |
| Water | 28.12 |
| U-care JR 30 | 0.2 |
| Panthenol | 1.0 |
| BZT | 0.18 |
| Silicone fluid (DC245) | 0.5 |
| Procetyl 10 (PPG-10, cetyl ether) | 0.5 |
| Farnesol | 0.5 |
| Phenoxyethanol | 0.5 |
| (B) Alcohol surgical hand prep-2 | |
| Ethanol | 68 |
| Babassuamidopropalkonium Chloride | 0.5 |
| Water | 27.97 |
| U-care JR 30 | 0.2 |
| Panthenol | 1.0 |
| BZT | 0.18 |
| Silicone fluid (DC245) | 0.5 |
| Procetyl 10 (PPG-10, cetyl ether) | 0.5 |
| Farnesol | 0.5 |
| Phenoxyethanol | 0.5 |
| PHMB | 0.15 |
| (C) Alcohol surgical hand prep-3 | |
| Ethanol | 68 |
| Babassuamidopropalkonium Chloride | 0.5 |
| Water | 28.12 |
| U-care JR 30 | 0.2 |
| Panthenol | 1.0 |
| BZT | 0.18 |
| Silicone fluid (DC245) | 0.5 |
| Procetyl 10 (PPG-10, cetyl ether) | 0.5 |
| Farnesol | 0.25 |
| Geranium oil | 0.25 |
| Phenoxyethanol | 0.5 |
| (D) Pre-op skin disinfectant-1 | |
| Ethanol | 60 |
| Povidone iodine | 7.5 |
| Water | 31.07 |
| U-care JR 30 | 0.2 |
| BZT | 0.18 |
| CHG | 0.05 |
| Farnesol | 0.5 |
| Phenoxyethanol | 0.5 |

FORMULATIONS WITH ZINC SALTS

General Formula

| Ingredients | Percent range (w/w) |
|---|---|
| Ethanol | 50-90 |
| Water | 15-35 |
| U-care polymers | 01.-0.5 |
| Germall + | 0.15-0.3 |
| Quaternary ammonium compounds | 0.05-0.2 |
| Quaternary conditioners | 0.2-1.0 |
| Emollients | 0.3-2.0 |
| Phenoxyethanol (if present) | 0.5-1.0 |
| Silicone fluids | 0.0-1.0 |
| Essential oils/individual ingredients | 0.3-1.0 |
| Biguanides (if present) | 0.05-2.0 |
| Zinc gluconate | 0.3-0.6 |
| Zinc acetate | 0.1-0.3 |
| Zinc lactate | 0.1-0.3 |

Specific formulas

| Ingredients | Percent (w/w) |
|---|---|
| (E) Alcohol hand disinfectant-1 | |
| Ethanol | 60 |
| Babassuamidopropalkonium Chloride | 0.3 |
| Water | 36.23 |
| U-care JR 30 | 0.2 |
| Zinc acetate | 0.2 |
| Zinc gluconate | 0.3 |
| Zinc lactate | 0.1 |
| Panthenol | 1.0 |
| Chlorhexidine gluconate (CHG) | 0.05 |
| BZK | 0.12 |
| Silicone fluid (DC245) | 0.5 |
| Procety-10 (PPG-10 cetyl ether) | 0.5 |
| Farnesol | 0.5 |
| (F) Alcohol hand disinfectant-2 | |
| Ethanol | 60 |
| Babassuamidopropalkonium Chloride | 0.3 |
| Water | 36.08 |
| U-care JR 30 | 0.2 |
| Zinc acetate | 0.2 |
| Zinc gluconate | 0.3 |
| Zinc lactate | 0.1 |
| Panthenol | 1.0 |
| Chlorhexidine gluconate (CHG) | 0.05 |
| BZK | 0.12 |
| Silicone fluid (DC245) | 0.5 |
| Procety-10 (PPG-10 cetyl ether) | 0.5 |
| Farnesol | 0.5 |
| PHMB | 0.15 |
| (G) Alcohol surgical hand prep-1 | |
| Water | 26.87 |
| Zinc lactate | 0.2 |
| Zinc gluconate | 0.2 |
| Methocell K4MS | 0.1 |
| UcareJR 30 | 0.2 |
| Panthenol 50W | 1.0 |
| Ethanol | 68.0 |
| CrodamolSTS | 1.0 |
| Babassuamidopropalkonium Chloride | 0.3 |
| Procetyl 10 | 0.5 |
| PHMB | 0.15 |
| Farnesol | 0.3 |
| BZT | 0.18 |
| Propylene Glycol | 1.0 |
| (H) Alcohol surgical hand prep-2 | |
| Ethanol | 68 |
| Babassuamidopropalkonium Chloride | 0.5 |
| Water | 27.32 |
| U-care JR 30 | 0.2 |
| Zinc acetate | 0.2 |
| Zinc gluconate | 0.4 |
| Zinc lactate | 0.2 |
| Panthenol | 1.0 |
| BZT | 0.18 |
| Silicone fluid (DC245) | 0.5 |
| Procety-10 (PPG-10 cetyl ether) | 0.5 |
| Farnesol | 0.5 |
| Phenoxyethanol | 0.5 |
| (I) Alcohol surgical hand prep-3 | |
| Ethanol | 68 |
| Babassuamidopropalkonium Chloride | 0.5 |
| Water | 27.02 |
| U-care JR 30 | 0.2 |
| Zinc acetate | 0.2 |
| Zinc gluconate | 0.4 |
| Zinc lactate | 0.2 |

| | -continued | |
|---|---|---|
| Panthenol | | 1.0 |
| BZT | | 0.18 |
| Germall + | | 0.15 |
| Silicone fluid (DC245) | | 0.5 |
| Procety-10 (PPG-10 cetyl ether) | | 0.5 |
| Farnesol | | 0.5 |
| Phenoxyethanol | | 0.5 |
| PHMB | | 0.15 |
| (J) Alcohol surgical hand prep-3 | | |
| Ethanol | | 68 |
| Babassuamidopropalkonium Chloride | | 0.5 |
| Water | | 27.27 |
| U-care JR 30 | | 0.2 |
| Zinc acetate | | 0.2 |
| Zinc gluconate | | 0.4 |
| Zinc lactate | | 0.2 |
| Panthenol | | 1.0 |
| BZT | | 0.18 |
| Silicone fluid (DC245) | | 0.5 |
| Procety-10 (PPG-10 cetyl ether) | | 0.5 |
| Farnesol | | 0.5 |
| Phenoxyethanol | | 0.5 |
| CHG | | 0.05 |
| (K) Anti-irritant Surgical Hand Prep-4 | | Percentage (w/w) |
| Water | | 27.15 |
| Zinc lactate | | 0.2 |
| Zinc gluconate | | 0.2 |
| Methocell K4MS | | 0.1 |
| U Care-JR 30M | | 0.2 |
| D,L-Panthenol | | 0.5 |
| Benzethonium chloride | | 0.18 |
| Ethanol | | 68.0 |
| Crodamol STS | | 1.0 |
| Procetyl | | 0.5 |
| Babassuamidopropalkonium Chloride | | 0.3 |
| Propylene Glycol | | 1.0 |
| Farnesol | | 0.5 |
| Polyhexamethylene biguanide | | 0.15 |
| Fragrance | | 0.02 |
| (L) Anti-irritant Surgical Hand Prep-5 | | |
| Water | | 26.45 |
| Zinc lactate | | 0.2 |
| Zinc gluconate | | 0.2 |
| Klucell MCS | | 0.8 |
| U Care-JR 30M | | 0.2 |
| D,L-Panthenol | | 0.5 |
| Benzethonium chloride | | 0.18 |
| Ethanol | | 68.0 |
| Crodamol STS | | 1.0 |
| Procetyl | | 0.5 |
| Babassuamidopropalkonium Chloride | | 0.3 |
| Propylene Glycol | | 1.0 |
| Farnesol | | 0.5 |
| Polyhexamethylene biguanide | | 0.15 |
| Fragrance | | 0.02 |

(M) Alcohol Surgical Hand Prep Containing Zinc Gel

The following formulation is advantageously used by persons who wear latex gloves, but who have a latex allergy.

| Ingredients | Percent (w/w) |
|---|---|
| Ethanol | 68 |
| Babassuamidopropalkonium Chloride | 0.5 |
| Water | 22.93 |
| U-care JR 30 | 0.6 |
| Zinc acetate | 0.2 |
| Zinc gluconate | 0.7 |
| Zinc lactate | 0.2 |
| Zinc oxide | 2.0 |
| Panthenol | 1.0 |

| | -continued | |
|---|---|---|
| Ingredients | | Percent (w/w) |
| CHG | | 0.05 |
| Incroquat TMS Behenyl | | 0.5 |
| Silicone fluid (DC245) | | 0.5 |
| Procety-10 (PPG-10 cetyl ether) | | 0.5 |
| Glycerol | | 1.0 |
| Farnesol | | 0.5 |
| Germal Plus | | 0.2 |
| Phenoxyethanol | | 0.5 |
| Benzalkonium chloride | | 0.12 |
| (N) Alcohol based anti-irritant Surgical Prep | | |
| Water | | 26.87 |
| Zinc lactate | | 0.2 |
| Zinc gluconate | | 0.2 |
| Methocell K4MS | | 0.1 |
| UcareJR 30 | | 0.2 |
| Panthenol 50W | | 1.0 |
| Alcohol.SDA-40B | | 68.0 |
| CrodamolSTS | | 1.0 |
| Babassuamidopropalkonium Chloride | | 0.3 |
| Procetyl 10 | | 0.5 |
| PHMB | | 0.15 |
| Farnesol | | 0.3 |
| BZT | | 0.18 |
| Propylene Glycol | | 1.0 |
| (O) Topical cream-1 | | |
| Incroquat TMS Behenyl | | 0.8 |
| Polawax NF | | 0.8 |
| Petroleum Jelly | | 3.0 |
| Crothix | | 1.0 |
| Crodomol MM | | 1.0 |
| Cremerol HMG | | 1.0 |
| Propylene glycol | | 2.0 |
| Glycerin | | 8.0 |
| Water | | 78.22 |
| UCare JR30-M | | 0.2 |
| Germall Plus | | 0.2 |
| BZT | | 0.18 |
| Geranium oil | | 0.5 |
| Zinc acetate | | 0.2 |
| Zinc gluconate | | 0.7 |
| Zinc lactate | | 0.2 |
| Zinc oxide | | 2.0 |
| (P) Topical cream-2 | | |
| Incroquat TMS Behenyl | | 0.8 |
| Polawax NF | | 0.8 |
| Petroleum Jelly | | 3.0 |
| Crothix | | 1.0 |
| Crodomol MM | | 1.0 |
| Cremerol HMG | | 1.0 |
| Propylene glycol | | 2.0 |
| Glycerin | | 8.0 |
| Water | | 78.22 |
| UCare JR30-M | | 0.2 |
| Germall Plus | | 0.2 |
| BZT | | 0.18 |
| Basil Oil | | 0.5 |
| Zinc acetate | | 0.2 |
| Zinc gluconate | | 0.7 |
| Zinc lactate | | 0.2 |
| Zinc oxide | | 2.0 |
| (Q) Topical cream-3 | | |
| Incroquat TMS Behenyl | | 0.8 |
| Polawax NF | | 0.8 |
| Petroleum Jelly | | 3.0 |
| Crothix | | 1.0 |
| Crodomol MM | | 1.0 |
| Cremerol HMG | | 1.0 |
| Propylene glycol | | 2.0 |
| Glycerin | | 8.0 |
| Water | | 78.22 |
| UCare JR30-M | | 0.2 |
| Germall Plus | | 0.2 |

| Ingredients | Percent (w/w) |
|---|---|
| BZT | 0.18 |
| Sandalwood oil | 0.25 |
| Farnesol | 0.25 |
| Zinc acetate | 0.2 |
| Zinc gluconate | 0.7 |
| Zinc lactate | 0.2 |
| Zinc oxide | 2.0 |
| (R) Topical cream-4 | |
| Incroquat TMS Behenyl | 0.8 |
| Polawax NF | 0.8 |
| Petroleum Jelly | 3.0 |
| Crothix | 1.0 |
| Crodomol MM | 1.0 |
| Cremerol HMG | 1.0 |
| Propylene glycol | 2.0 |
| Glycerin | 8.0 |
| Water | 78.22 |
| UCare JR30-M | 0.2 |
| Germall Plus | 0.2 |
| BZT | 0.18 |
| Thyme oil | 0.5 |
| Zinc acetate | 0.2 |
| Zinc gluconate | 0.7 |
| Zinc lactate | 0.2 |
| Zinc oxide | 2.0 |
| (S) Pre-op skin disinfectant-1 | |
| Ethanol | 60 |
| Povidone iodine | 7.5 |
| Water | 30.47 |
| U-care JR 30 | 0.2 |
| Zinc acetate | 0.2 |
| Zinc gluconate | 0.3 |
| Zinc lactate | 0.1 |
| BZT | 0.18 |
| CHG | 0.05 |
| Farnesol | 0.5 |
| Phenoxyethanol | 0.5 |
| (T) Pre-op skin disinfectant-2 | |
| Ethanol | 60 |
| Povidone iodine | 2.0 |
| Water | 35.97 |
| U-care JR 30 | 0.2 |
| Zinc acetate | 0.2 |
| Zinc gluconate | 0.3 |
| Zinc lactate | 0.1 |
| BZT | 0.18 |
| CHG | 0.05 |
| Farnesol | 0.5 |
| Phenoxyethanol | 0.5 |
| (U) Pre-op skin disinfectant-3 | |
| Ethanol | 60 |
| Povidone iodine | 2.0 |
| Water | 35.52 |
| U-care JR 30 | 0.2 |
| Zinc acetate | 0.2 |
| Zinc gluconate | 0.3 |
| Zinc lactate | 0.1 |
| BZT | 0.18 |
| CHG | 0.5 |
| Farnesol | 0.5 |
| Phenoxyethanol | 0.5 |
| (V) Pre-op skin disinfectant-4 | |
| Ethanol | 60 |
| Povidone iodine | 2.0 |
| Water | 34.02 |
| U-care JR 30 | 0.2 |
| Zinc acetate | 0.2 |
| Zinc gluconate | 0.3 |
| Zinc lactate | 0.1 |
| BZT | 0.18 |
| CHG | 2.0 |
| Farnesol | 0.5 |
| Phenoxyethanol | 0.5 |
| (W) Zinc gel hand wash #1 | |
| UCare JR30-M | 0.05 |
| Methocel K100 | 0.1 |
| Water | 36.08 |
| Zinc gluconate | 0.3 |
| Zinc acetate | 0.1 |
| Zinc lactate | 0.1 |
| Germall Plus | 0.2 |
| Ethanol | 58 |
| Ispropanol | 2.0 |
| Silicone (Dimethicone) | 0.2 |
| Incroquat Behentyl TMS | 0.7 |
| Polawax A31 | 0.3 |
| Glycerin | 1.0 |
| Cetyl ether (PPG10) | 0.5 |
| CHG | 0.05 |
| BZK | 0.02 |
| Farnesol | 0.3 |
| (X) Zinc Gel Hand Wash#2 | |
| Water | 33.45 |
| Ethanol | 62.0 |
| Farnesol | 0.3 |
| Propylene glycol | 1.0 |
| Polyhexamethylene biguanide | 0.15 |
| Babassuamidopropalkonium Chloride | 0.3 |
| Procetyl-10 (PPG-10 Cetyl ether | 0.5 |
| Crodamol STS | 1.0 |
| BZT | 0.1 |
| Zinc lactate | 0.2 |
| Zinc gluconate | 0.2 |
| D,L-Panthenol | 0.5 |
| UCare JR 30M | 0.2 |
| Methocel K4MS | 0.1 |
| (Y) Zinc gel cream/lotion for under latex gloves | |
| Ucare JR30-M | 0.8 |
| Methocel K100 | 0.3 |
| Water | 26.63 |
| Zinc gluconate | 0.6 |
| Zinc acetate | 0.2 |
| Zinc lactate | 0.2 |
| Germall Plus | 0.2 |
| Zinc stearate | 1.5 |
| Zinc oxide | 1.0 |
| Glucate DO | 5.0 |
| Ethanol | 55.0 |
| Isopropanol | 3.0 |
| Silicone (Dimethicone) | 0.5 |
| Incroquat Behenyl TMS | 1.0 |
| Polawax A31 | 0.5 |
| Glycerin | 2.0 |
| Cetyl ether (PPG10) | 1.0 |
| CHG | 0.05 |
| BZK | 0.02 |
| Farnesol | 0.3 |
| Vitamin E | 0.2 |
| (Z) Anti-irritant disinfectant soap | |
| Polyox WSR 205 | 0.1 |
| UCare Jr30-M | 0.2 |
| Germall Plus | 0.2 |
| Water | 86.93 |
| Pluronic F87 | 2.0 |
| Cocoamidopropylbetaine | 1.0 |
| Mirapol A-15 | 1.0 |
| Propylene glycol | 2.0 |
| Polyquaternium-47(Merquat 3330) | 3.0 |
| Glycerin | 2.0 |
| CHG | 0.05 |
| BZK | 0.12 |
| Triclosan | 0.3 |
| Farnesol | 0.3 |

-continued

| Ingredients | Percent (w/w) |
|---|---|
| Lemon oil | 0.3 |
| Zinc acetate | 0.1 |
| Zinc lactate | 0.1 |
| Zinc gluconate | 0.3 |

6. WORKING EXAMPLES

6.1. Example 1

Topical formulations containing zinc salts as anti-irritants were prepared in the presence and absence of EO and IC and in the presence and absence of antimicrobial compounds, such as benzalkonium chloride (BZK), chlorhexidine gluconate (CHG), zinc pyrithione (ZP) and triclosan (TC). The following EO and IC were evaluated: lemon oil as a representative essential oil, farnesol and linalool as representative terpene alcohols, and citral as a representative aldehyde. The resulting formulations then were evaluated for their antimicrobial activity.

6.1.1. Method

Preparation of Alcohol Based Zinc Gel

An alcohol based gel was prepared as follows, and the antimicrobials, EOs and/or ICs were added to this base:

| BASE #1 | |
|---|---|
| Ingredient | % by weight |
| UCare JR30-M | 0.1 |
| Methocel K100 | 0.1 |
| Water | 36.4 |
| Zinc gluconate | 0.3 |
| Zinc acetate | 0.1 |
| Zinc lactate | 0.1 |
| Germall Plus | 0.2 |
| Ethanol | 58 |
| Isopropanol | 2.0 |
| Silicone (Dimethicone) | 0.2 |
| Incroquat Behenyl TMS | 0.7 |
| Polawax A31 | 0.3 |
| Glycerin | 1.0 |
| Cetyl ether (PPG10) | 0.5 |

Evaluation of Rapid Antimicrobial Activity in Presence of Serum

To determine the efficacy of the antimicrobial composition on the skin, which may be contaminated with blood or other proteinaceous fluids containing bacteria, the antimicrobial activity was evaluated in the presence of serum as follows. Briefly, 0.5 ml of $10^8$ CFU of S. aureus/ml was added to 0.5 ml of bovine adult serum in a sterile culture tube and mixed. 0.5 ml of the test formulation was added to each tube and vortexed. After 15 seconds, it was further diluted 1:100 with drug inactivating media (LTSB) and 0.5 ml was plated on a TSA plate. The plates were incubated at 37° C. for 24 hours and the colony count per ml of culture was determined.

6.1.2. Results

It was observed that farnesol, linanool, citral and lemon oil showed synergistic antimicrobial effects when combined with BZK. No such synergism was observed when farnesol was combined with other antimicrobial compounds, CHG, ZP or TC. See Table 1 below.

TABLE 1

Synergistic effect of EO and IC ingredients with antimicrobial agents Test organism: S. aureus

| Group | CFU/mL | $Log_{10}$ reduction |
|---|---|---|
| Control (Base) | $3.4 \times 10^7$ | — |
| BZK | $5.4 \times 10^5$ | 1.8 |
| CHG | $6.6 \times 10^5$ | 1.7 |
| TC | $1.5 \times 10^6$ | 1.3 |
| ZP | $1.4 \times 10^6$ | 1.4 |
| F | $8.4 \times 10^6$ | 0.6 |
| LI | $1.5 \times 10^6$ | 1.3 |
| CI | $1.5 \times 10^6$ | 1.3 |
| LO | $1.6 \times 10^6$ | 1.3 |
| BZK + F | $3.0 \times 10^2$ | 5.0 |
| BZK + CI | $2.0 \times 10^2$ | 5.2 |
| BZK + LI | $6.0 \times 10^2$ | 4.7 |
| BZK + LO | $1.4 \times 10^3$ | 4.4 |
| CHG + BZK + F | $2.3 \times 10^2$ | 5.2 |
| CHG + BZK + LO | $1.4 \times 10^3$ | 4.4 |
| CHG + BZK + LI | $2.0 \times 10^2$ | 5.2 |
| CHG + BZK + CI | $1.0 \times 10^2$ | 5.5 |
| CHG + BZK + LO + TC | $1.4 \times 10^3$ | 4.4 |
| CHG + BZK + F + TC | $1.5 \times 10^2$ | 5.3 |
| CHG + BZK + F + ZP + LO | $2.0 \times 10^2$ | 5.2 |
| CHG + LO | $1.6 \times 10^5$ | 2.3 |
| TC + LO | $1.4 \times 10^6$ | 1.4 |
| ZP + LO | $1.4 \times 10^6$ | 1.4 |
| CHG + F | $6.8 \times 10^4$ | 2.7 |
| TC + F | $1.2 \times 10^6$ | 1.4 |
| ZP + F | $1.3 \times 10^6$ | 1.4 |

Key:
BZK: Benzalkonium chloride (0.12%);
PHMB: Polyhexamethylenebiguanide hydrochloride (0.15%);
CHG: Chlorhexidene gluconate (0.05%);
TC: Triclosan (0.3%);
ZP: Zinc pyrithione (0.5%);
F: Farnesol (0.3%);
LO: Lemon oil (0.3%);
LI: Linalool; (0.3%);
CI: Citral (0.3%)

It can be seen from Table 1 that, among the antimicrobial compounds used, only the quaternary ammonium compound, benzalkonium chloride, exhibited significant synergistic activity in combination with EOs and ICs.

6.2. Example 2

The present example shows the antimicrobial activity of compositions comprising a quaternary ammonium compound, benzethonium chloride (BZT) and farnesol in the presence and absence of zinc salts. The antimicrobial activity was evaluated as described in Example 1.

Famesol and BZT were incorporated into Base #1 (containing zinc salts) and Base #2 (not containing zinc salts) shown below in proportions shown in Table 2.

| BASE #2 (Without zinc salts) | |
|---|---|
| Ingredient | % by weight |
| UCare JR30-M | 0.1 |
| Methocel K100 | 0.1 |
| Water | 36.9 |
| Germall Plus | 0.2 |
| Ethanol | 58 |
| Ispropanol | 2.0 |
| Silicone (Dimethicone) | 0.2 |
| Incroquat Behenyl TMS | 0.7 |
| Polawax A31 | 0.3 |

-continued

| BASE #2 (Without zinc salts) | |
|---|---|
| Ingredient | % by weight |
| Glycerin | 1.0 |
| PPG-10 Cetyl ether (Procetyl-10) | 0.5 |

TABLE 2

Test organism: *S. aureus*

| | Without zinc salts | | With zinc salts | |
|---|---|---|---|---|
| Quantity in Gel (% w/w) | cfu/ml | $\log_{10}$ reduction | cfu/ml | $\log_{10}$ reduction |
| Control Gel | $4.1 \times 10^7$ | 0.0 | $1.4 \times 10^7$ | 0.0 |
| BZT (0.18%) | $7.5 \times 10^5$ | 1.7 | $3.3 \times 10^5$ | 1.6 |
| Farnesol (0.5%) | $8.9 \times 10^5$ | 1.7 | $4.5 \times 10^5$ | 1.5 |
| BZT (0.18%) + Farnesol (0.5%) | $2.0 \times 10^2$ | 5.4 | $6.7 \times 10^1$ | 5.3 |

These results demonstrate the synergistic antimicrobial effects of BZT and farnesol, which occur both in the presence or absence of zinc salts.

6.3. Example 3

The antimicrobial effects of varying proportions of farnesol and quaternary ammonium compounds, incorporated into Base #2, were evaluated using the same method described in Example 1. The results are shown in Table 3.

TABLE 3

Test organism: *S. aureus*

| Groups in Gel Base (% w/w) | cfu/ml | $\log_{10}$ reduction |
|---|---|---|
| Control Gel | $1.4 \times 10^7$ | 0.0 |
| BZT (0.18%) (preservative level) | $3.3 \times 10^5$ | 1.6 |
| BZT (0.12%) | $4.7 \times 10^5$ | 1.5 |
| BZT (0.06%) | $5.7 \times 10^5$ | 1.4 |
| BZK (0.12%) (preservative level) | $5.4 \times 10^5$ | 1.4 |
| BZK (0.06%) | $1.8 \times 10^6$ | 0.9 |
| Farnesol (0.5%) | $4.5 \times 10^5$ | 1.5 |
| Farnesol (0.3%) | $4.6 \times 10^5$ | 1.5 |
| BZT (0.18%) + Farnesol (0.5%) | $6.7 \times 10^1$ | 5.3 |
| BZT (0.18%) + Farnesol (0.3%) | $6.7 \times 10^1$ | 5.3 |
| BZT (0.12%) + Farnesol (0.3%) | $1.0 \times 10^2$ | 5.1 |
| BZT (0.06%) + Farnesol (0.3%) | $1.0 \times 10^2$ | 5.1 |
| BZK (0.12%) + Farnesol (0.5%) | $2.0 \times 10^2$ | 4.8 |
| BZK (0.12%) + Farnesol (0.3%) | $3.7 \times 10^3$ | 3.6 |
| BZK (0.06%) + Farnesol (0.3%) | $7.9 \times 10^3$ | 3.2 |

These results demonstrate that both quaternary ammonium compounds, BZK and BZT, exhibit synergistic antimicrobial activity when used in combination with farnesol on *S. aureus* in a rapid serum-based assay.

6.4. Example 4

The antimicrobial effects of various EO and IC, in the presence or absence of quaternary ammonium compounds, BZK and BZT, incorporated into Base #2, were evaluated using the same assay described in Example 1. The amounts of various agents used are presented in Table 4. In addition to *S. aureus*, the rapid assay was also performed with *E. coli*. The results are shown in Table 4.

TABLE 4

| | *S. aureus* | | *E. coli* | |
|---|---|---|---|---|
| Group | cfu/ml | $\log_{10}$ reduction | cfu/ml | $\log_{10}$ reduction |
| Control (Base) | $1.4 \times 10^7$ | 0.0 | $2.6 \times 10^7$ | 0.0 |
| BZK | $3.3 \times 10^5$ | 1.6 | $5.8 \times 10^5$ | 1.6 |
| BZT | $5.3 \times 10^5$ | 1.4 | $4.3 \times 10^5$ | 1.8 |
| Farnesol | $4.5 \times 10^5$ | 1.5 | $4.3 \times 10^5$ | 1.8 |
| Patchouli oil | $2.0 \times 10^6$ | 0.8 | $2.0 \times 10^6$ | 1.1 |
| Basil oil | $1.4 \times 10^6$ | 1.0 | $6.2 \times 10^4$ | 2.6 |
| Eucalyptus oil | $1.6 \times 10^6$ | 0.9 | $1.9 \times 10^6$ | 1.1 |
| Thyme oil | $1.3 \times 10^6$ | 1.0 | $4.9 \times 10^5$ | 1.7 |
| Clove oil | $1.6 \times 10^6$ | 0.9 | $1.4 \times 10^5$ | 2.3 |
| Geranium oil | $3.8 \times 10^6$ | 0.6 | $8.0 \times 10^4$ | 2.5 |
| Orange oil | $6.9 \times 10^6$ | 0.3 | $4.9 \times 10^5$ | 1.7 |
| Mullein oil | $6.1 \times 10^5$ | 1.4 | $6.2 \times 10^5$ | 1.6 |
| Citronella oil | $4.7 \times 10^5$ | 1.5 | $2.2 \times 10^5$ | 2.1 |
| Sandalwood oil | $7.4 \times 10^5$ | 1.3 | $4.9 \times 10^5$ | 1.7 |
| Farnesol + BZK | $2.0 \times 10^2$ | 4.8 | $3.4 \times 10^4$ | 2.9 |
| Farnesol + BZT | $5.3 \times 10^2$ | 4.4 | $6.8 \times 10^4$ | 2.6 |
| Patchouli oil + BZT | $6.7 \times 10^1$ | 5.3 | $1.1 \times 10^4$ | 3.4 |
| Basil oil + BZT | $3.3 \times 10^1$ | 5.6 | $6.7 \times 10^1$ | 5.6 |
| Eucalyptus oil + BZT | $3.3 \times 10^1$ | 5.6 | $4.2 \times 10^3$ | 3.8 |
| Thyme oil + BZT | $3.3 \times 10^1$ | 5.6 | $3.3 \times 10^1$ | 5.9 |
| Clove oil + BZT | $3.3 \times 10^1$ | 5.6 | $2.0 \times 10^2$ | 5.1 |
| Geranium oil + BZT | $3.3 \times 10^1$ | 5.6 | $3.3 \times 10^1$ | 5.9 |
| Orange oil + BZT | $3.3 \times 10^3$ | 3.6 | $3.5 \times 10^4$ | 2.9 |
| Mullein oil + BZT | $2.4 \times 10^5$ | 1.8 | $9.8 \times 10^4$ | 2.4 |
| Citronella oil + BZT | $6.7 \times 10^2$ | 5.3 | $2.8 \times 10^3$ | 4.0 |
| Sandalwood oil + BZT | $2.0 \times 10^2$ | 4.8 | $4.7 \times 10^3$ | 3.7 |

Key:
BZK: Benzalkonium chloride (0.12% w/w: preservative level);
BZT: Benzethonium chloride (0.18% w/w: preservative level);
all other EO/IC (0.5% w/w).

These results demonstrate that various essential oils, when used in combination with quaternary ammonium compounds, exhibit rapid synergistic antimicrobial activity on *S. aureus* in a rapid serum-based assay. In particular, patchouli oil, basil oil, eucalyptus oil, thyme oil, clove oil, geranium oil, and citronella oil show pronounced antimicrobial effects.

6.5. Example 5

The effect of the addition of various biguanide antimicrobial compounds to combinations of farnesol and quaternary ammonium compound, incorporated into Base #2 was tested using the assay described in Example 1. The results are shown in Table 5.

TABLE 5

| | *S. aureus* | | *E. coli* | |
|---|---|---|---|---|
| Group | cfu/ml | $\log_{10}$ reduction | cfu/ml | $\log_{10}$ reduction |
| Gel base | $1.4 \times 10^7$ | 0.0 | $2.6 \times 10^7$ | 0.0 |
| CHG (0.05%) | $6.6 \times 10^5$ | 1.3 | $4.8 \times 10^5$ | 1.7 |
| BZT (0.18%) | $5.3 \times 10^5$ | 1.4 | $4.3 \times 10^5$ | 1.8 |
| PHMB (0.15%) | $4.3 \times 10^4$ | 2.9 | $6.0 \times 10^5$ | 1.6 |
| Farnesol (0.5%) | $4.5 \times 10^5$ | 1.5 | $4.3 \times 10^5$ | 1.8 |
| Farnesol (0.5%) + CHG (0.05%) | $6.8 \times 10^4$ | 2.3 | $7.2 \times 10^4$ | 2.5 |
| Farnesol (0.5%) + PHMB (0.15%) | $2.7 \times 10^3$ | 4.1 | $6.5 \times 10^2$ | 4.6 |
| Farnesol (0.5%) + BZT (0.18%) | $5.3 \times 10^2$ | 4.4 | $6.8 \times 10^4$ | 2.6 |
| Farnesol (0.5%) + BZT (0.18%) + CHG (0.05%) | $5.0 \times 10^2$ | 4.5 | $2.0 \times 10^2$ | 5.1 |

TABLE 5-continued

| Group | S. aureus | | E. coli | |
|---|---|---|---|---|
| | cfu/ml | log₁₀ reduction | cfu/ml | log₁₀ reduction |
| Farnesol (0.5%) + BZT (0.18%) + PHMB (0.15%) | $3.0 \times 10^2$ | 5.0 | $1.0 \times 10^2$ | 5.4 |

PHMB appears to enhance the activity of the combination of BZT and farnesol.

6.6. Example 6

This example demonstrates the antimicrobial activity of gels comprising farnesol in combination with various antimicrobial agents. The concentrations of the antimicrobial agents were selected in keeping with the permissible levels of these ingredients in leave-on skin care formulations. The antimicrobial activity was assayed using the method described in Example 1 using Gel Base #1. The data has been presented in Table 6.

TABLE 6

Test organism: S. aureus

| Ingredients in the Gel (% w/w) | Recommended range as preservatives (% w/w) | log₁₀ reduction in colony count from the control[a,b] |
|---|---|---|
| Farnesol (0.3%) | — | 0.6 |
| CHG (0.05%) | 0.0-0.05 | 1.7 |
| PHMB (0.15%) | 0.1-0.3 | 2.9 |
| TC (0.3%) | 0.3-0.5 | 1.3 |
| BZT (0.18%) | 0.1-0.2 | 1.6 |
| BZK (0.12%) | 0.1-0.12 | 1.8 |
| Farnesol (0.3%) + CHG (0.05%) | — | 2.7 |
| Farnesol (0.3%) + PHMB (0.15%) | — | 3.4 |
| Farnesol (0.3%) + TC (0.3%) | — | 1.4 |
| Farnesol (0.3%) + BZT (0.18%) | — | 5.3 |
| Farnesol (0.3%) + BZK (0.12%) | — | 5.0 |

[a]The colony count of the Control Base experiment was $3.4 \times 10^7$ cfu/ml.
[b]For Control, the same Gel Base as used for the Gels shown in Table 6, but without any antimicrobial agents.

The results show that farnesol's ability to enhance the activity of the antimicrobial agents ranges from compound to compound. Farnesol shows synergy with the quaternary ammonium compounds, benzalkonium chloride (BZT) and benzethonium chloride (BZK). Among biguanide antimicrobial compounds, it enhances the activity of polyhexamethylene biguanide hydrochloride (PHMB), but not that of chlorhexidine gluconate (CHG). Farnesol also does not show any synergy with triclosan, nor does it enhance triclosan's action. Therefore, the ability of farnesol to show synergy or enhance the action of biocides/preservatives is specific to the antimicrobial agents in question.

A similar study was performed using the same concentration of farnesol above in Table 6 (0.3% w/w, i.e. 1.35 mM per 100 g gel) and the various antimicrobial agents were added to the gel in the same molar concentration (0.06 mM per 100 g of gel). The data has been presented in Table 7 below.

TABLE 7

Test organism: S. aureus

| Ingredients in the Gel (gram millimoles per 100 g Gel) | log₁₀ reduction in colony count from the control[a,b] |
|---|---|
| Farnesol (1.35 mM) | 1.8 |
| CHG (0.06 mM) | 1.9 |
| PHMB (0.06 mM) | 2.1 |
| TC (1.04 mM)[c] | 1.3 |
| BZT (0.06 mM) | 1.9 |
| Farnesol (1.35 mM) + CHG (0.06 mM) | 2.0 |
| Farnesol (1.35 mM) + PHMB (0.06 mM) | 3.2 |
| Farnesol (1.35 mM) + TC (1.04 mM)[c] | 1.4 |
| Farnesol (1.35 mM) + BZT (0.06 mM) | 5.5 |

[a]The colony count of the Control Base experiment was $6.4 \times 10^7$ cfu/ml.
[b]For Control, the same Gel Base as used for the Gels shown in Table 7 but without any preservatives/biocides was used.
[c]Since Triclosan is not effective even at 1.04 mM concentration, experiment was not performed with 0.06 mM concentration.

Similar to the results shown in Table 6, farnesol has a varying effect on enhancement of the antimicrobial activity of the various antimicrobial agents. Farnesol appears to exhibit synergistic antimicrobial activity in combination with BZT, but not with triclosan. PHMB appears to enhance the acitivity of farnesol. The mechanism of farnesol to show synergy or enhance the activity of the antimicrobial agents varies for different compounds, but is the same for the same compound, irrespective of the concentration (whether the compound is taken in % w/w or in molar proportions).

Various references, patents, publications, product descriptions, etc., are cited throughout this specification, the disclosures of which are incorporated herein by reference in their entireties for all purposes.

What is claimed is:

1. An antimicrobial composition for topical use comprising a quaternary ammonium benzethonium chloride compound present at a concentration of between 0.01 and 0.5% (w/w), a polyhexamethyl biguanide, an individual constituent of an essential oil present at a concentration of between 0.05 and 1.0 percent (w/w), and two or more zinc salts in an amount that reduces irritation, wherein the quaternary ammonium benzethonium chloride compound, the polyhexamethyl biguanide, and the individual constituent of an essential oil are present in amounts which exhibit synergistic antimicrobial activity, and wherein the polyhexamethyl biguanide is present at a concentration of between 0.1 to 2.0% w/w.

2. The composition of claim 1, wherein the individual constituent of an essential oil is selected from the group consisting of 1-citronellol, α-amylcinnamaldehyde, lyral, geraniol, farnesol, hydroxycitronellal, isoeugenol, eugenol, eucalyptol, linalool and citral.

3. The composition of claim 1, wherein the zinc salts are selected from the group consisting of zinc gluconate and zinc lactate.

4. The composition of claim 1, wherein the zinc salts are each present at a concentration of between 0.1% and 0.5% w/w.

5. The composition of claim 1, further comprising panthenol present at a concentration of between 0.5% and 2% w/w.

6. The composition of claim 1, further comprising alcohol present at a concentration of between 10-90% w/w, water present at a concentration of between 15-70% w/w, thickeners and/or gelling agents present at a concentration of between 0.05-3.0% w/w, and emollients present at a concentration of between 0.1-3.0% w/w.

7. An antimicrobial composition for topical use comprising a quaternary ammonium benzethonium chloride compound present at a concentration of between 0.01 and 0.5% (w/w), between 0.1 to 2.0% (w/w) of a polyhexamethyl biguanide, between 0.05 and 1.0 percent (w/w) farnesol, and two or more zinc salts in an amount that reduces irritation, wherein the quaternary ammonium benzethonium chloride compound, the polyhexamethyl biguanide, and the farnesol are present in amounts which exhibit synergistic antimicrobial activity.

* * * * *